(12) United States Patent
Kuo

(10) Patent No.: US 8,788,285 B2
(45) Date of Patent: Jul. 22, 2014

(54) CLINICAL DATA FILE

(75) Inventor: Eric E. Kuo, Foster City, CA (US)

(73) Assignee: Align Technology, Inc., San Jose, CA (US)

( * ) Notice: Subject to any disclaimer, the term of this patent is extended or adjusted under 35 U.S.C. 154(b) by 1891 days.

(21) Appl. No.: 11/888,695

(22) Filed: Aug. 2, 2007

(65) Prior Publication Data
US 2009/0037222 A1 Feb. 5, 2009

(51) Int. Cl.
*G06Q 50/00* (2012.01)
*G06F 19/00* (2011.01)
*G06Q 50/24* (2012.01)

(52) U.S. Cl.
CPC .............. *G06F 19/322* (2013.01); *G06Q 50/24* (2013.01); *G06F 19/321* (2013.01)
USPC .................................................. 705/3; 705/2

(58) Field of Classification Search
None
See application file for complete search history.

(56) References Cited

U.S. PATENT DOCUMENTS

| | | | | |
|---|---|---|---|---|
| 2002/0169635 | A1* | 11/2002 | Shillingburg | 705/2 |
| 2003/0154108 | A1* | 8/2003 | Fletcher-Haynes et al. | 705/3 |
| 2005/0075544 | A1* | 4/2005 | Shapiro et al. | 600/300 |
| 2005/0114283 | A1* | 5/2005 | Pearson et al. | 706/50 |
| 2005/0159984 | A1* | 7/2005 | Hirano et al. | 705/3 |
| 2005/0182654 | A1* | 8/2005 | Abolfathi et al. | 705/2 |
| 2007/0016441 | A1* | 1/2007 | Stroup | 705/2 |
| 2007/0174079 | A1* | 7/2007 | Kraus | 705/1 |
| 2007/0192715 | A1* | 8/2007 | Kataria et al. | 715/764 |
| 2007/0242069 | A1* | 10/2007 | Matsue et al. | 345/428 |
| 2008/0319942 | A1* | 12/2008 | Courdy et al. | 707/3 |

OTHER PUBLICATIONS

Microsoft—About Drawing Objects and pictures—Microsoft Office Excel 2003, Feb. 28, 2011.*
Microsoft—Overview of secuirty an protection in Excel—Microsoft Office Excel 2003, Feb. 28, 2011.*
Microsoft—Secure a workbook with a password—Microsoft Office Excel 2003, Feb. 28, 2011.*
Microsoft—Secure documents and files—Microsoft Office Excel 2003, PowerPoint 2003, Word 2003, Feb. 28, 2011.*
Microsoft—Insert a scanned or digital picture—Microsoft Office Excel 2003, Feb. 28, 2011.*
Microsoft—Import and modify pictures Feb. 28, 2011.*

* cited by examiner

*Primary Examiner* — Neal Sereboff
(74) *Attorney, Agent, or Firm* — Brooks, Cameron & Huebsch, PLLC

(57) ABSTRACT

Embodiments are provided for a patient data file menu and methods for creating the same. One embodiment includes a number of patient medical information items including a data type label and a position in a data file menu, a sequence of one or more tabs, where each tab represents a stage in a procedure, and where the patient medical information items are associated with the tab corresponding to the stage in the procedure to which the patient medical information item corresponds, treatment professional information in a treatment professional profile section of the file, and patient personal information in a patient profile section of the file.

31 Claims, 2 Drawing Sheets

CLINICAL DATA FILE

BACKGROUND

The present disclosure relates to devices and methods for treatment planning. More particularly, the present disclosure is related to a data file using a data format for medical information.

An orthodontic treatment process can use corrective appliances such as braces and/or other fixed or removable appliances to bring the teeth, lips, and jaws into proper alignment and to achieve a facial balance. However, in determining the orthodontic treatment process, information can be gathered in many different file formats. For example, three-dimensional images, digital and/or analog images, and/or digital and/or analog video can be taken of a patient's mouth. Also, text files can be generated, including notes, comments, prescription notes, and/or medical history.

In some instances, it is beneficial when planning an orthodontic treatment process to confer and discuss various possible treatment routes with other treatment professionals (e.g., specialists, other orthodontists, and/or the restorative dentist). However, it can be difficult to meet with a multitude of treatment professionals at a single location. In addition, although patient data can now be sent almost instantaneously over the Internet, difficulties arise in viewing and sending multiple types of files because this may require each treatment professional to have special software for each type of file, with keeping patient personal information secure and confidential, with treatment professionals ability to see all of the content and to see it as intended, and/or with contents of sent files being presented in an understandable manner.

DETAILED DESCRIPTION

According to the present disclosure, systems, and methods are provided for converting clinical data to a single format and creating a patient data file including the clinical data in the single format, among other embodiments. As used herein, "clinical data" refers to data generated in the process of treating a patient.

For example, clinical data can include, but is not limited to, patient medical information items including x-rays, three-dimensional (3-D) models of a dental patient's mouth, and/or digital and/or analog pictures of the patient's teeth. In addition, clinical data can include prescription notes and/or treatment professional comments in text, audio, and/or video clip format.

Clinical data can also include other information generated when forming a treatment plan for the patient. For example, other information can include information that is generated in instances where the treatment plan is to reposition the patient's teeth with a number of incremental stages using a plurality of custom appliances to move teeth by discrete movements.

Embodiments of the present disclosure can be used to provide information in an organized and coherent manner. For example, in some embodiments, a user interface can be utilized that includes a number of tabs (e.g., like electronic versions of labeled tabs on electronic file folders or other information) that can be used to organize items that can be accessed by a user.

Embodiments can provide a mechanism for transferring information from one place to another (e.g., from one treatment professional to another, from one treatment office to another, etc.) For instance, data can be created or converted to a clinical data format which can be used to transfer information in a format that may be available by both, the sender and the recipient.

In some embodiments, methods of the present disclosure can be carried out by instructions stored in memory and executed by a processor in a computing device. The instructions can, for example, be included in a computer readable medium. In such embodiments, a computer readable medium can be any medium that can store computer readable information thereon. Suitable examples include optically or magnetically readable forms of media, among others.

Figure 1:
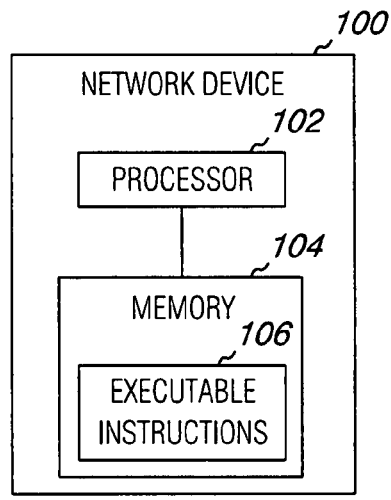
FIG. 1 illustrates a computing device embodiment to perform the methods of the present disclosure.

FIG. 1 illustrates a computing device embodiment to perform the methods of the present disclosure. In some embodiments, the computing device 100 can be used to create a patient data file. In the computing device embodiment of FIG. 1, the device 100 includes one or more processors 102 in communication with one or more memory locations 104.

The memory 104 can include a number of instructions 106 that can be executed on the processor 102. Memory 104 can also include one or more items of data that can be used in the execution of the instructions 106 by the processor 102. The instructions 106 can be executed by the processor 102 to cause the computing device 100 to perform a method of the present disclosure, as described herein.

Figure 2:
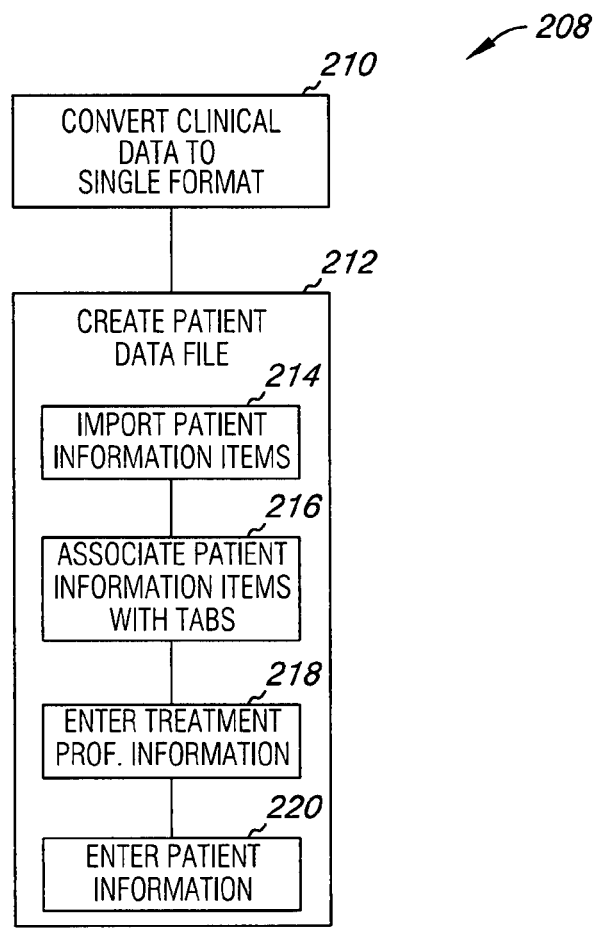
FIG. 2 illustrates the method for creating a patient data file according to embodiments of the present disclosure.

FIG. 2 illustrates a method for creating a patient data file according to embodiments of the present disclosure. Unless explicitly stated, the method embodiments described herein are not constrained to a particular order or sequence. Additionally, some of the described method embodiments can occur or be performed at the same point in time.

As illustrated at block 210, the method 208 includes converting clinical data to a single format. In some embodiments, the conversion of clinical data can include converting all clinical data to a single format that is a different format than the clinical data is created in originally. In some embodiments, the conversion of clinical data can include converting a portion of the clinical data to a single format, where some clinical data is currently in the single format.

As illustrated at block 212, the method 208 includes creating a patient data file 212 including the clinical data. As illustrated, creating the patient data file 212 can include several steps. For example, at block 214, patient medical information items (e.g., patient images) can be imported into the patient data file.

At block 216, the patient medical information items can be associated with a tab in a sequence of one or more tabs. Each tab can represent a stage in a procedure, and the patient medical information items can be associated with the tab corresponding to the stage in the procedure to which the patient medical information item corresponds.

In some embodiments, each stage in the procedure represented by a tab can be a time period. For example, for a twenty-four month treatment process, each tab can represent a two-week time period, giving at least fifty-two tabs in the patient data file.

In some embodiments, the patient medical information items can be manually associated with the tab corresponding to the stage in the procedure to which the patient medical information item corresponds by a user. In various embodiments, the patient medical information items can be associated with the tab corresponding to the stage in the procedure to which the patient medical information item corresponds automatically by instructions stored in the memory and executed by the processor.

For example, the instructions can be executed by the processor to associate the patient medical information item with a tab based on when the patient medical information item was created or when the patient medical information item was saved. Other criteria for associating the patient medical information items with the tabs can also be utilized in some embodiments.

As discussed herein, in some embodiments patient medical information items can include several different types of patient images including x-ray images, two or three-dimensional images, and/or digital and/or analog images, among others. However, in some instances the various patient images can be created in many different file formats, making it difficult to view all of the patient images without having specific software for each file format. By importing the patient images into the patient data file after the clinical data (e.g., patient images) has been provided (e.g., converted) in a single file format, the patient images can be viewed using a single file viewer enabled by a single software application.

The many different types of patient images can include, for example, facial anterior (repose), facial anterior (smiling), profile (repose), profile (smiling), right buccal, left buccal, anterior intraoral, upper occlusal, lower occlusal, close-up smile, individual teeth, patient medical/dental history, patient diagnosis, a three-dimensional (3-D) model of the patient's mouth (e.g., ClinCheck 3-D model, Invisalign® proprietary software that illustrates the movement of teeth), full mouth series x-rays, panoramic x-rays, cephalometric x-rays, and/or individual radiographs such as periapicals, bitewings, and/or occlusals, two-dimensional (2-D) computed tomography (CT) radiographic slices, and 3-D CT radiographs, among others.

Since the patient images can include many different types of images, in some embodiments, creating the patient data file 212 can include labeling the imported patient images according to data type (e.g., profile (smiling)). In addition, in some embodiments, creating the patient data file 212 can include positioning at least one patient image in a data file menu, as discussed further herein. For example, the patient images can be positioned in a descending order of importance according to a treatment professional. In some embodiments, instructions can be executed by the processor to put the imported images into a default position in the data file menu.

In some embodiments, at least one patient image can be represented by a thumbnail on the data file menu. In such embodiments, instructions can include instructions executed by the processor, where selecting the thumbnail of the patient image can access an enlarged patient image.

As illustrated at block 218, creating the patient data file includes entering the treatment professional information into a treatment professional profile section. Treatment professional information can include, but is not limited to, treatment professional name, office address, office contact information (e.g., telephone number, fax number, electronic mail address), office logo, treatment professional photograph, practice mission statement, and/or treatment professional resume highlights, among other items.

Also, as illustrated at block 220, creating the patient data file 212 can include entering patient personal information into a patient profile section. The patient profile section can, for example, include, patient name, address, contact information (e.g., telephone number, fax number, electronic mail address), date of birth, gender, and/or dental insurance, among others.

In some embodiments, the method can include instructions executed by the processor to embed a pass code into the patient data file once the patient data file is saved in memory. For example, the pass code can be used to restrict viewing of some information (e.g., text/images, time based information), some files, and/or restrict transfer and/or modification of such information/files.

The pass code, for example, can be a password known to the user. The pass code can alternatively be an identifier associated with a computing device, such as an identifier uniquely associated with the computing device or network when the patient data file is saved.

Further, the method can include instructions that are executed by the processor to allow the patient data file to be modified after the pass code is entered into the computing device. By embedding a pass code into the patient data file and preventing modifications to the patient data file without the pass code, the patient data file can be viewed by a number of users, however, only authorized users can modify the patient data file. In addition, limiting modification ability can help to maintain the authenticity and integrity of the patient data file.

In some embodiments, once the patient data file has been created and saved, additional patient images can be imported. In various embodiments, an additional tab can be added to the sequence of one or more tabs and the additional patient images can be associated with the additional tab. In such embodiments, the process of importing additional patient images and associating the additional patient images with an additional tab in the sequence of one or more tabs can be repeated throughout the treatment process.

Allowing the addition of more tabs and patient images as the treatment process continues can serve to organize the patient data file or files by associating patient images created later in a treatment process with a later tab. Thus, a treatment professional can see the progress of the treatment process by viewing the patient images in each tab in progression rather than trying to sift through various patient images created at various times.

In addition, associating patient information with an additional tab as the treatment process continues creates uniformity in the organization of the patient images and other clinical data. For example, without the use of tabs, a treatment professional or other user could organize the patient data file in a first way, whereas another treatment professional could organize the patient data file in a second way. However, by associating the patient information with a tab, the patient information is associated with the tab corresponding to the stage in the procedure to which the patient information corresponds, and a treatment professional is limited to organizing the patient information within the tab.

In embodiments where the patient data file includes an embedded pass code, as discussed herein, the additional patient images and additional tab can be added and saved to the patient data file without entering the pass code. This can allow a new treatment professional to add new patient images to the patient data file, while preventing alteration of previous medical history information. In some embodiments, the additional patient images and additional tabs can be added only after the pass code has been entered.

Once the patient data file has been created and saved, instructions can be executed by the processor to view the patient data file on a display. Viewing the patient data file can include viewing the data file menu and/or the treatment professional profile, among other things, as discussed herein.

Figure 3:
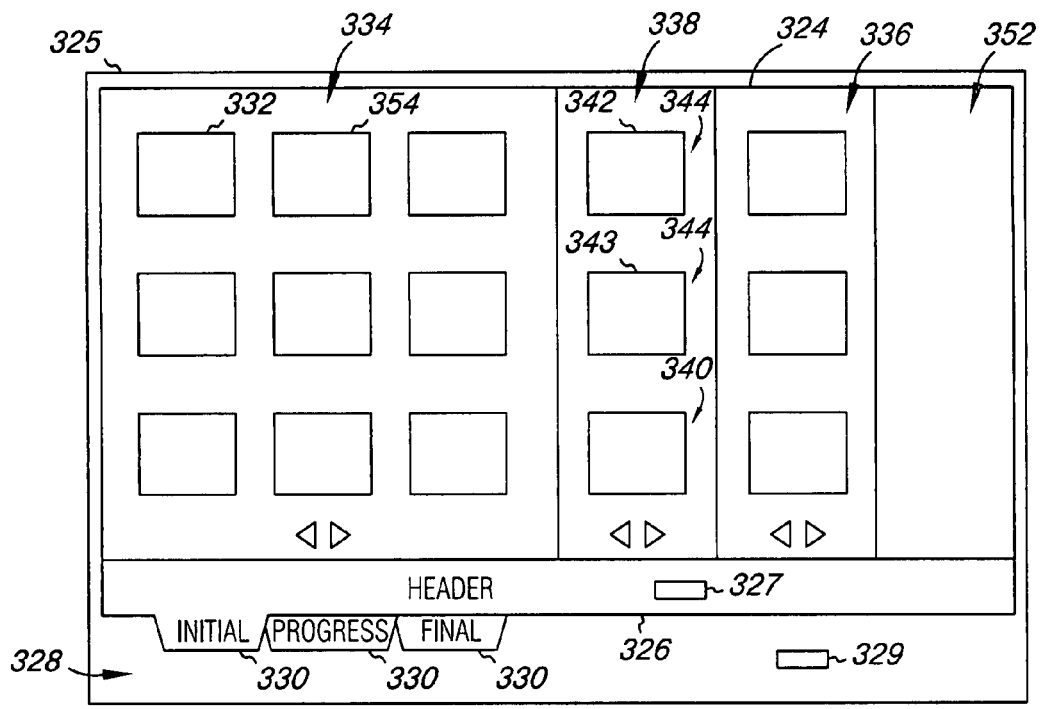
FIG. 3 is an illustration of a data file menu on a display according to embodiments of the present disclosure.

FIG. 3 is an illustration of a data file menu 324 on a display 325 according to embodiments of the present disclosure. The data file menu 324 can include a header 326 displaying various patient personal information, such as a patient's name and age, among other items. For example, in some embodiments, the header 326 can display a patient's initials to maintain a patient's privacy.

The header 326 can also include a patient personal information icon 327. When the patient personal information icon 327 is selected, instructions can be executed by the processor to view the patient profile section, as discussed herein. As discussed herein, patient personal information can include patient's name, gender, and/or age, among other items. Patient personal information can be used to determine and/or consult on the treatment process. For example, the treatment process for a fourteen year old patient can differ from the treatment process for a forty year old patient, making the age of the patient useful for the treatment professional viewing the patient data file.

In addition, the data file menu 324 can include a treatment professional information icon 329. Similarly, when the treatment professional icon 329 is selected, instructions can be executed by the processor to view the treatment professional profile section, as discussed herein.

As discussed herein, the treatment professional profile can include treatment professional information such as office contact information, practice mission statement, and/or professional resume highlights. In some instances, a treatment professional can send the patient data file to potential patients to show the progress of previous patients. In such embodiments, the treatment professional profile section can, for example, aid the potential patient in determining whether the potential patient selects the treatment professional.

In other instances, a treatment professional can send the patient data file to a second treatment professional for consultation. In such instances, the treatment professional profile can aid the second treatment professional in determining whether to consult with the treatment professional, and to what extent the second treatment professional should consult with the treatment professional.

In addition, as discussed herein, in some embodiments, the patient data file can be created with an embedded pass code. In such embodiments, the patient personal information in the patient profile section and/or treatment professional information in the treatment professional profile section can be viewed upon entering the pass code, otherwise the patient personal information and/or treatment professional information remains hidden.

In the embodiment of FIG. 3, the data file menu 324 also includes a sequence 328 of one or more tabs 330, as discussed herein. When a tab 330 is selected, instructions can be executed by the processor to display the patient images 332 that are associated with the tab 330.

In some embodiments, the patient images 332 can be separated into sections on the data file menu 324. For example, as shown in FIG. 3, patient images 332 that are photographs can be in a photograph section 334, patient images 332 that are x-rays can be in an x-ray section 336, and a third section 338 can include 3-D models 340 and text information 344.

In some embodiments, the text information 344 can be free text 342. In addition, as discussed herein, patient images 332 can include patient medical/dental history. In some embodiments, the patient medical/dental history can be a text image 343 that is associated with the tab 330 corresponding to the stage in the procedure to which the text image corresponds. In addition, in some embodiments, the data file menu 324 can include a comment section 352, as discussed further herein.

As discussed herein, in some embodiments, at least one patient image 332 can be associated with a thumbnail 354. As shown in FIG. 3, the data file menu 324 can include thumbnails 354 of the patient images 332 so that more images can be seen at one time. In some embodiments, the thumbnails 354 can be selected and instructions can be executable by a processor to enlarge the patient image 332.

Figure 4:
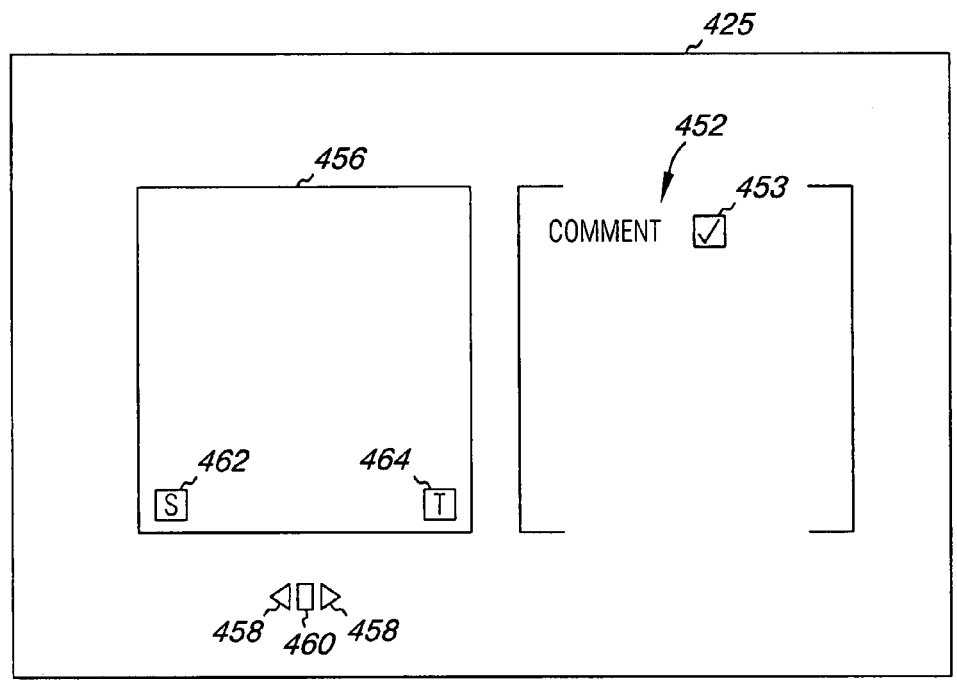
FIG. 4 is an illustration of a display of an enlarged patient image according to embodiments of the present disclosure.

FIG. 4 is an illustration of a display 425 of an enlarged patient image 456 according to embodiments of the present disclosure. In some embodiments, the display can include navigation arrows 458, where instructions can be executed by the processor to advance the enlarged patient image 456 from one image to the next patient image associated with the same tab as the displayed enlarged patient image 456 in the data file menu.

Instructions can also be executed to go back to the previous patient image associated with the same tab as the displayed enlarged patient image 456 in the data file menu, as discussed herein, when one of the navigation arrows 458 are selected. The display 425 can also include a menu shortcut 460, where instructions can be executed by the processor to return to the data file menu 324 (e.g., FIG. 3) when selected.

In some embodiments, a stitch icon 462 can be included in the display 425 of the enlarged patient image 456. In some embodiments, once the stitch icon 462 is selected, instructions can be executed by the processor to view enlarged patient images 456 having a specific data type when one of the navigation arrows 458 are selected.

For example, if the enlarged patient image 456 on the display 425 has a data type of "close-up smile" and the stitch icon 462 is selected, the next patient image having the data type "close-up smile" can be displayed when one of the navigation arrows 458 are selected. In other words, using the stitch icon 462 can allow a user to view patient images from each tab in the sequence of one or more tabs having the specific data type without having to select the menu shortcut 460 to go back to the data file menu to select a different tab. Using the stitch icon 462 can also allow the user to view patient images having a specific data type from each tab without having to advance through every patient image associated with each tab.

The stitch function can also be accomplished without using a stitch icon 462. For example, the data file menu can include a drop-down menu, where a data type can be selected from a list of possible data types. In some embodiments, the stitch function can be activated when a user, for example, double-clicks the enlarged patient image 456.

As illustrated in FIG. 4, the display of the enlarged patient image 456 can include a comments section 452 as discussed herein. In some embodiments, when the thumbnail of a patient image is selected, instructions can be executed by a processor to enlarge the patient image, as shown in FIG. 4, and to display comments associated with the patient image in the comment section 452. In some embodiments, a patient image can include notations on the image. In some embodiments, a comment in the comment section 452 can explain the notation on the image.

In some embodiments, when the patient data file is created and the patient images are imported, a user (e.g., treatment professional) can modify the patient image by highlighting an area, by circling an aspect and/or area, and/or by blacking out an area to protect the patient's privacy. Blacking out an area of a patient image can help a treatment professional hide identifying characteristics of a patient.

This functionality can allow a treatment professional to send the patient data file to a second treatment professional for a second opinion without losing doctor-patient confidentiality. It can also decrease the need for additional documentation between the treatment professional, patient, and second treatment professional regarding permission to view the patient data file. In some embodiments, the user can include a comment in the comment section 452 explaining the modification.

In some embodiments, the data file menu comment section (e.g., comment section 352 in FIG. 3) can include a list of comments such as comments regarding modifications to images and comments made by a treatment professional when creating and/or viewing the patient data file, as discussed herein. In some embodiments, the comment section illustrated in FIG. 4 can include the list of comments displayed in the comment section on the data file menu.

In various embodiments, the comment section illustrated in FIG. 4 can include just the one or more comments associated with the enlarged patient image 456, as discussed herein. In some embodiments, the user can choose between viewing the entire list of comments from the data file menu or the comments associated with the enlarged patient image 456, or can select comments to be viewed.

As shown in FIG. 4, the enlarged patient image 456 can include a toolbar 464 for modifying the enlarged patient image 456. When the toolbar 464 is selected, instructions executed by the processor can cause tools to appear, such as, text tools, fill tools, and/or draw tools, including circle, square, pen size selection, and/or color selection, among others. An exit tool can also appear when the toolbar 464 is selected, in some embodiments. In such embodiments, once the tools appear, a user can modify the enlarged patient image 456 to highlight an area of interest and/or to make a notation on the enlarged patient image 456, among other modifications.

Once the user is finished, the user can select the exit tool and instructions executable by the processor can save the modifications. In addition, a user can enter comments into the comment section 452, as discussed herein, explaining the modifications and/or inquiring about a portion of the enlarged patient image 456.

Other types of comments can also be entered into the comment section 452. For example, in some embodiments, instructions executable by the processor can save the modifications and/or the comments entered into the comment section 452 separate from the enlarged patient image 456. In addition, by entering comments into the comment section 452 with the enlarged patient image 456, instructions executed by the processor can associate the comments with the enlarged patient image 456 displayed when the one or more comments are entered.

As discussed herein, in some embodiments, the comments entered into the comment section 452 with the enlarged patient image 456 can also be seen on the patient data file menu in the comment section as a discussion thread. In embodiments where the comments entered are associated with the enlarged patient image 456 displayed when the comment is entered, a tag 453 can be inserted next to the comment into the comment section 452 with the enlarged patient image 456 as well as next to the comment in the comment section on the patient data file.

As used herein, the tag 453 refers to an icon, where the icon can be a graphic picture (e.g., a pencil), and/or a textual hyperlink. In such embodiments, instructions can be executed by a processor to enlarge to a preset and/or user-established dimension and/or view, the modified patient image associated with the comment when the tag 453 is selected.

In some embodiments, the tag can be used to show appended draw elements to help direct visual attention towards important area(s) of an image. The tag may also be associated with an audio file that, for example, is recorded in association with a view, comment, and/or image. In some embodiments, more than one modified patient image can be enlarged when multiple tags 453 are selected.

As discussed herein, in some embodiments, a treatment professional can send the patient data file to a second treatment professional for a second opinion. In some embodiments, the second treatment professional can modify the enlarged patient images 456 and/or insert comments.

In such embodiments, by associating a tag with a comment when the comment is inserted after the enlarged patient image 456 is modified, the treatment professional can view the enlarged patient images 456 directly from the data file menu by selecting the tag 453 associated with the comment. This can help the treatment professional follow the order in which the second treatment professional viewed the patient data file, facilitating greater understanding of the second opinion and the thought process to form the second opinion.

In some embodiments, once the user is finished modifying the enlarged patient image 456 and/or entering comments into the comment section 452 and selects the exit tool, instructions can be executed by the processor to secure the comments and/or modifications from further modification. In some embodiments, the comments and/or modifications can be modified after entering a pass code into the computing device.

In some embodiments, instructions are executed by the processor to send the patient file to a second computing device. In various embodiments, the patient data file can be sent to a second user, as discussed herein, where the user can view the patient data file on the same computing device, a second computing device, or a non-networked computing device by transport of one or more files on a portable computing device readable medium.

For example, the patient data file can be sent from a first treatment professional to a second treatment professional via the Internet. The second treatment professional can then open and view the patient data file on a display at any computing device that includes a computing device readable medium having instructions which can be executed by a processor to cause a computing device to view the patient data file.

In some embodiments, once the patient data file is received, instructions which can be executed by a processor can cause the computing device to view the patient data file menu (e.g., as shown in FIG. 3), on a display 425. The patient data file menu can include, for example, one or more thumbnails of patient images, one or more tabs in a sequence of tabs, one or more comment sections, patient personal information, and/or treatment professional information, as discussed herein. In addition, a thumbnail can be selected to enlarge the patient image.

In such embodiments, the treatment professional or other user who receives the patient data file can use the tool bar 464 to modify one or more enlarged patient images 456, and/or can enter comments into the comment section 452. As discussed herein, a tag 453 can be inserted next to the comment in the comment section 452 when the comment is associated with the enlarged patient image 456 that is modified and/or that is displayed when the comment is entered. The treatment professional or other user can repeat this process for as many patient images as desired.

As discussed herein, the modifications and comments can be saved separately from the enlarged patient images 456. In such embodiments, the treatment professional, or other user, can send the modifications and comments to the computing device that the patient data file was received from and/or to another computing device or save to a fixed or portable computing device readable medium. When the original computing device and/or different computing device receives the modifications and/or comments, instructions can be executed by the processor to allow the receiving user to accept or reject the modifications and/or comments.

In embodiments where the receiving computing device includes the patient data file, accepting the modifications and/or comments can cause instructions executed by the processor to save the modifications and/or comments and merge them with the patient data file. In embodiments where the receiving computing device does not include the patient data file, accepting the modifications and/or comments can cause instructions executed by the processor to save the modifications and/or comments as well as the entire patient data file. In some embodiments, the user sending the modifications and/or comments can choose whether to send the modifications, comments, and/or the entire patient data file.

By saving the modifications and/or comments separately from the enlarged patient images 456, the enlarged patient image 456 as well as the patient data file can be maintained in the form in which it was created. This can help to prevent unintended and/or unauthorized modifications to the patient data file. Allowing the user to accept or reject modifications and/or comments can also help to prevent unauthorized modifications.

In some embodiments, more than one treatment professional, or other user, can send modifications and/or comments to the original treatment professional. In such embodiments, when the modifications and/or comments are accepted, instructions executed by the processor can cause more than one set of modifications and/or comments to be merged with the patient data file. In such embodiments, the different sets of modifications and/or comments can be displayed with an identifier to indicate the sender. For example, each treatment professional, or other user, sending modifications and/or comments can be assigned a different color, identifier, and/or font.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A method for presenting medical information, comprising:
    receiving a number of patient medical information items including a data type label via a computing device, where at least one of the number of patient medical information items comprises a patient image, where the at least one patient image includes a blacked out area to protect the patient's privacy;
    converting the number of patient medical information items to a single data format that is different than an original data format of at least one of the number of patient medial information items via the computing device;
    importing the number of converted patient medial information items to a patient data file via the computing device;
    associating each of the number of patient medial information items with one of a sequence of one or more tabs via the computing device, where each tab represents a stage in an orthodontic treatment process, and where the patient medical information items are associated with the tab corresponding to the stage in the orthodontic treatment process to which each of the number of patient medical information items corresponds;
    importing treatment professional information into a treatment professional profile section of the data file via the computing;
    importing receiving patient personal information into a patient profile section of the data file via the computing device;
    restricting access to at least one of a first portion of the patient personal information and a second portion of the treating professional information by embedding a pass code into the data file via the computing device; and
    displaying a first patient medical information item of a particular data type associated with a first tab via the computing device; and
    displaying a second patient medical information item of the particular type associated with a second tab in response to an input via the computing device, where the input indicates a request to view patient medical information items of the particular data type, and where the input does not specify a tab.

2. The method of claim 1 further comprising modifying the data file to include an additional tab in the sequence of one or more tabs corresponding to an additional stage in the orthodontic treatment process and additional patient medical information items associated with the additional tab.

3. The method of claim 2, where the data file is unmodifiable except for the addition of the additional tab corresponding to the additional stage in the orthodontic treatment process and the additional patient medical information items.

4. The method of claim 1 further comprising associating the patient medical information items with the tab corresponding to the stage in the orthodontic treatment process to which the patient medical information items correspond by a user.

5. The method of claim 1 further comprising associating the patient medical information items with the tab corresponding to the stage in the orthodontic treatment process to which the patient medical information items correspond automatically based on the stage in the orthodontic treatment process in which the images were created.

6. The method of claim 1 further comprising associating the patient medical information items with the tab according to the stage in the orthodontic treatment process to which the patient medical information items correspond automatically based on the stage in the orthodontic treatment process in which the information items were saved.

7. The method of claim 1, where each stage in the orthodontic treatment process is a time period.

8. The method of claim 1, further including text information, where the text information is at least one of free text in a free text section of the patient file and an image with text associated with the tab corresponding to the stage in the orthodontic treatment process to which the text image corresponds.

9. The method of claim 1, where the patient medical information items include notations on the patient medical information items.

10. The method of claim 1, where at least one patient medical information item is a three-dimensional representation of a dental patient's mouth.

11. The method of claim 1, where the data file menu includes a thumbnail of at least one of the patient medical information items.

12. A computing device readable medium having executable instructions which can be executed by a processor to cause a computing device to perform a method, comprising:
receiving clinical data in a plurality of data formats;
converting the clinical data to a single data format that is different than at least one of the plurality of formats;
creating a patient data file, including the clinical data in the single data format, where creating the patient data file includes:
importing patient images into the patient data file, where the patient images each include a data type, and where at least on patient image includes a blacked out area to protect the patient's privacy;
associating each of the patient images with a tab in a sequence of one or more tabs, the tab corresponding to a stage in an orthodontic treatment process to which the patient image corresponds;
importing treatment professional information into a treatment professional profile section;
importing patient personal infollnation into a patient profile section;
restricting access to at least one of a first portion of the patient personal information and a second portion of the treating professional information by embedding a pass code into the patient data file; and
saving the patient data file;
displaying a first patient image of a particular data type associated with a first tab; and
displaying a second patient image of the particular data type associated with a second tab in response to an input, where the input indicates a request to view patient images of the particular data type, and where the input does not specify a tab.

13. The medium of claim 12, where the method includes labeling the patient images according to data type.

14. The medium of claim 12, where the method includes positioning at least one patient image in a data file menu.

15. The medium of claim 12, where the method includes:
adding additional patient images; and
associating the additional patient images with an additional tab in the sequence of one or more tabs.

16. The medium of claim 12, where the method includes modifying the patient data file after entering the pass code into the computing device.

17. A computing device comprising:
a processor;
a memory connected to the processor: and
executable instructions storable in the memory and executable by the processor to:
receive clinical data in a plurality of data formats;
convert the clinical data to a single data format that is different than at least one of the plurality of data formats;
import patient images into a patient data file, where the patient images each include a data type, and where at least one patient image includes a blacked out area to protect the patient privacy;
associate the patient images with a tab in a sequence of one or more tabs, where the patient images are associated with the tab corresponding to a stage in an orthodontic treatment process to which the patient image corresponds;
import treatment professional information into a treatment professional profile section of the patient data file;
import receive patient personal information into a patient profile section of the patient data file;
restrict access to at least one of a first portion of the patient personal information and a second portion of the treating professional information by embedding a pass code into the patient data file;
save the patient data file; and
display a first patient image of a particular data type associated with a first tab; and
display a second patient image of the particular data type associated with a second tab in response to an input, where the input indicates a request to view patient images of the particular data type, and where the input does not specify a tab.

18. The computing device of claim 17, where the executable instructions include instructions to send the patient data file to a second computing device.

19. The computing device of claim 17, where the executable instructions include instructions to position the patient images in a data file menu, where the data file menu includes a thumbnail of at least one of the patient images.

20. The computing device of claim 19, where the executable instructions include instructions to select the thumbnail of the patient images to access an enlarged patient image.

21. The computing device of claim 17, where the executable instructions include instructions to:
label the patient images according to data type; and
view the patient images in the sequence of one or more tabs according to data type on a display.

22. A computing device readable medium having executable instructions which can be executed by a processor to cause a first computing device to perform a method, comprising:
receiving a patient data file from a second computing device, where the second computing device displays a user interface including a sequence of one or more tabs, where each tab represents a stage in an orthodontic treatment process;

displaying the patient data file, where the patient data file includes at least one of a thumbnail of a patient image, the one or more tabs in the sequence of tabs, a comment section, patient personal information, and treating professional information:

displaying an unrestricted portion of the patient data file before a pass code is received into the patient data file;

receiving the pass code into the patient data file;

displaying the unrestricted portion of the patient data file and the restricted portion of the data file in response to receiving the pass code;

in response to the patient data file menu including the thumbnail, receiving a thumbnail selection to enlarge the patient image, where the enlarged patient image is of a particular data type, is associated with a first tab. and includes a blacked out area to protect the patient's privacy;

receiving an input indicating a request to view patient images of the particular data type where the input does not specify a tab;

in response to receiving the input, displaying a second patient image of the particular data type associated with a second tab;

in response to the patient data file menu including the comment section, displaying comments in the comment section; and in response to the patient data file menu including the thumbnail and the comment section:
modifying the enlarged patient image; and
associating at least one comment with the modified enlarged patient image.

23. The medium of claim 22, where, in response to the patient data file menu including one or more tabs in the sequence of tabs, the patient data file includes a number of patient images associated with the tabs in the sequence of tabs, and where, in response to the patient data file menu including the thumbnail. the patient images include a data type label and a position on the patient data file menu.

24. The medium of claim 23, where the method includes:
specifying a patient image first data type in response to the patient data file menu including the thumbnail; and
displaying a sequence of patient images associated with the tabs in the sequence of tabs with the first data type label in response to the patient data file menu including the thumbnail and the one or more tabs in a sequence of tabs.

25. The medium of claim 23, where the method includes displaying the number of patient images according to each patient image position on the patient data file menu.

26. The medium of claim 22, where associating at least one comment with the modified enlarged patient image includes inserting a tag with the at least one comment in the comment section.

27. The medium of claim 26, where selecting the tag causes executable instructions to select the modified enlarged patient image.

28. The medium of claim 22, where modifying the enlarged patient image includes saving the modifications to the enlarged patient image separate from the enlarged patient image.

29. The medium of claim 28, where the method includes sending the modifications to the enlarged patient image and the comments in the comment section to at least one of a third computing device and the first computing device.

30. The medium of claim 29, where the method includes receiving the modifications to the enlarged patient image and the comments in the comment section at the computing device and merging the modifications and comments with the patient data file.

31. The medium of claim 22, where, in response to the patient data file menu including the comment section, the method includes protecting the comments in the comment section with a pass code.

* * * * *

UNITED STATES PATENT AND TRADEMARK OFFICE
CERTIFICATE OF CORRECTION

PATENT NO.        : 8,788,285 B2
APPLICATION NO.   : 11/888695
DATED             : July 22, 2014
INVENTOR(S)       : Eric E. Kuo Page 1 of 1

It is certified that error appears in the above-identified patent and that said Letters Patent is hereby corrected as shown below:

In the claims

Column 10, line 24, delete "medial" and insert -- medical --, therefor

Column 10, line 27, delete "medial" and insert -- medical --, therefor

Column 10, line 38, delete "receiving", therefor

Column 11, line 42, delete "on" and insert -- one --, therefor

Column 11, line 50, delete "infollnation" and insert -- information --, therefor Column 12, line 21, delete "patient" and insert -- patient's --, therefor Column 12, line 30, delete "receive", therefor Signed and Sealed this
Seventh Day of October, 2014

Michelle K. Lee
*Deputy Director of the United States Patent and Trademark Office*